United States Patent [19]
Levin et al.

[11] Patent Number: 6,031,233
[45] Date of Patent: Feb. 29, 2000

[54] HANDHELD INFRARED SPECTROMETER

[75] Inventors: Kenneth H. Levin, Silver Spring; Samuel Kerem, Rockville; Vladimir Madorsky, Reisterstown, all of Md.

[73] Assignee: Infrared Fiber Systems, Inc., Silver Spring, Md.

[21] Appl. No.: 09/033,304

[22] Filed: Mar. 2, 1998

Related U.S. Application Data

[63] Continuation-in-part of application No. PCT/US96/14128, Aug. 30, 1996
[60] Provisional application No. 60/003,047, Aug. 31, 1995.

[51] Int. Cl.[7] .................................................. G01N 21/35
[52] U.S. Cl. ............................... 250/339.11; 250/339.12; 356/51; 356/326
[58] Field of Search .......................... 250/339.11, 339.12, 250/339.07, 341.8, 504 H; 356/51, 328

[56] References Cited

U.S. PATENT DOCUMENTS

| | | |
|---|---|---|
| 4,043,668 | 8/1977 | Goetz et al. . |
| 4,527,062 | 7/1985 | Novinson . |
| 4,560,275 | 12/1985 | Goetz . |
| 4,883,963 | 11/1989 | Kemeny et al. . |
| 5,120,961 | 6/1992 | Levin et al. . |
| 5,216,484 | 6/1993 | Chao et al. ............................. 356/226 |
| 5,319,437 | 6/1994 | Kemeny et al. . |

FOREIGN PATENT DOCUMENTS 9702481  1/1997  WIPO .

OTHER PUBLICATIONS

Casayet al., "Long–wavelength fluorescence probes–chemistry and semiconductor laser: A diffcult marriage" SPIE, vol. 2138, pp.228–240, (1994).

*Primary Examiner*—Constantine Hannaher
*Assistant Examiner*—Albert Gagliardi
*Attorney, Agent, or Firm*—Browdy and Neimark

[57] ABSTRACT

A handheld device for infrared reflectance measurements of samples for identification of the sample materials is a self-contained portable unit built into a handheld housing. The housing includes a window and optics on a bench adjacent the window, so that the optics will be aligned with the sample when the device is placed directly against the sample. The optics include a broad-band IR light source (ordinary lamp) shining onto an acousto-optic tunable filter (AOTF), which passes narrow-band IR light with a swept frequency; a lens focussing the IR through the window onto the sample; and a reflectance detector aligned with the window of the housing to pick up reflected light. A computer, which may be mounted in the housing, compares the detected reflectance spectrum with stored sample data spectra, and identifies the material or the components of the material and their proportions. Inclusion of all the parts inside the housing allows the device to be portable; this is made possible by the alignment of the lamp, AOTF filter, lens, window, and detector, which has high optical efficiency, and by elimination of optical fibers.

25 Claims, 5 Drawing Sheets

HANDHELD INFRARED SPECTROMETER

CROSS-REFERENCE TO RELATED APPLICATION

This application is a continuation-in-part of PCT application no. PCT/US96/14128, filed Aug. 30, 1996, designating the United States, which claims the benefit of U.S. Provisional Application No. 60/003,047, filed on Aug. 31, 1995. The entire contents of both of said applications are hereby incorporated herein by reference.

FIELD OF THE INVENTION

The present invention relates to devices for analyzing a material according to its optical reflectance or transmission spectrum.

BACKGROUND OF THE INVENTION

Plastics and many other materials can be identified by their infrared (IR) reflectance or transmission spectrum. Each type—nylon, polyethylene, etc.—has its own IR characteristic spectrum. If a generally constant-intensity IR beam incident on a plastic is scanned through a range of wavelengths, and the intensity of the reflected or transmitted light is measured as a function of the wavelength, then the measured spectrum can be used to identify the type of plastic.

In addition, mixtures of plastics or other materials can be quantitatively analyzed. The reflectance or transmission spectrum of a sample can show that it is, for example, 50% nylon and 50% polyethylene. The proportion of octane in a sample of gasoline can be measured, or the amount of fat in a chocolate bar.

Several types of IR spectrometers are known. Some use diffraction grating or FTIR technology; these are bulky, delicate, and slow. They are not suited to rapid identification of plastics, use in various locations such as in the field, or for handheld use.

Another known type uses an acousto-optical tunable filter (AOTF) such as that disclosed in U.S. Pat. No. 5,120,961 to Levin et al, U.S. Pat. No. 4,883,963 to Kemeny et al, and U.S. Pat. No. 4,052,121 to Chang, the entire contents of which patents are fully incorporated herein by reference. The acousto-optic tunable filter (AOTF) is based on a birefringent crystal, such as a crystal of $TeO_2$ (tellurium dioxide) which acts as an electronically tunable narrowband filter, in which diffraction results from an acoustic pressure wave in the crystal.

If an acoustic wave traverses the crystal, the compression or pressure inside the crystal varies as the wave passes, causing a periodic variation in the refractive index. As crystal compression varies, so does the birefringence of a beam of unpolarized visible light or IR that passes through the crystal in a direction normal to its entry and exit faces. When sound having a certain acoustic wavelength is present in the crystal, the crystal acts as an optical filter passing that light or infrared having a wavelength proportional to the acoustic wavelength. Because the birefringent crystal acts as a frequency-selective narrowband optical filter, and sound of any acoustic wavelength can be passed through the crystal, any desired visible or IR wavelength can be selected at will, just by varying the frequency of an acoustic driver.

The acoustic driver is a second crystal of the piezo-electric type (quartz or lithium niobate, LiNbo), which is an acoustic transducer. Such a piezo crystal changes its size when subjected to an RF field.

Birefringent $TeO_2$ bonded to piezo-electric LiNo, in which the LiNo is subjected to a sinusoidally-varying AC voltage applied across the face parallel to the birefringent crystal, will act as a swept-frequency optical filter. When the AC voltage impressed across the piezo crystal is at high radio-frequencies (RF) of 20–100 MHz, the acoustic wavelength corresponds to infrared (IR) light wavelengths. (One MHz is one million cycles per second.) The impressed voltage may be obtained from digital synthesizer, controlled by a software algorithm which determines the frequencies generated, and which can sequentially scan or hop in a random access fashion.

Broad-spectrum white light (from a halogen lamp, for example) which shines through the crystal (parallel to the junction between the birefringent and piezo crystals) will emerge as a beam having one optical frequency corresponding to the acoustic frequency of sound in the piezo crystal. Typical IR wavelengths selected by the AOTF filter are from 1–3 $\mu$m (near infrared) or from 2–5 $\mu$m (mid-infrared).

The tuned infrared beam can then be either reflected from, or transmitted through, a sample to determine the spectrum and identification of the sample. To identify the sample of plastic or other material, the swept-frequency beam of light is made to shine onto a surface of the undetermined material, which will reflect different proportions of the light falling onto it at each of the various frequencies. A photodetector can be used to pick up the reflected light and turn it into an electrical signal. Electronic circuits can then plot the pattern of the material's reflectance of IR or light frequency, and use that pattern to identify the material by matching the pattern with known patterns corresponding to various materials.

IR spectrometers can measure the proportion of a compound in a sample, by calibrating the circuitry to recognize samples having various percentages of compounds. The percentage can also be calculated according to Beer's law.

Compared to other spectrometer instruments such as diffraction gratings and the FTIR, the AOTF spectrometer has the advantages of no moving parts, high speed wavelength tuning, and small size. However, previous AOTF spectrometers have consisted of a fairly bulky and heavy electronics and optical modules, so that the instrument cannot be portable and handheld or low cost. In addition, for measurement of remote samples in-situ, it has been necessary to use fiber optics to pass the light between the instrument and the sample.

In these conventional AOTF systems the IR coming out of the AOTF is passed into an optical fiber or bundle of fibers, which traps the light and passes it along the bundle, but with substantial loss, especially at longer IR frequencies. (Optical fibers can pass visible light with little attenuation, but IR is strongly absorbed.) The end of the fiber or bundle can then be placed near the surface of the material, and reflected light picked up by other fibers of the bundle to be conveyed back to a photo-detector.

While the optical-fiber arrangement allows the light-emitting end to be placed easily at any point, it has several drawbacks in addition to the aforementioned inefficiency in transporting IR. First, optical fibers are expensive. Second, they are fragile. Third, the coupling between a light source, such as the lamp/AOTF, and the fiber is very inefficient. Only a small fraction of the available light can be conveyed into and along the fibers. Furthermore, because optical fibers are quite small the light they convey scatters widely from their ends, and is dispersed, so still more light is lost even if the end of the fiber bundle is placed almost against the surface of the material under test.

The high losses of optical fibers require a very bright lamp in front of the AOTF, of 50 to 100 W. These high wattage lamps typically require cooling fans. The high-wattage lamps and fans in turn require a larger power supply, and the larger power supply may require heat dissipating fin plates or fans of its own, which then draw still more power and increase the size and bulk still further. The frame or housing must be larger and heavier to support the additional parts. Expense is increased and portability decreased.

Prior-art AOTF spectrometers are locked into a "catch-22" size and weight restriction. The bulk of the lamp/AOTF units prevents them from being held up to a sample, so fiber optics are used to convey the IR from the housing to the sample; but since fibers waste energy, the housing must be large and heavy. Previous workers in the field have not achieved a portable AOTF spectrometer because they have not realized the root of the size/weight problem.

Another, related drawback of conventional AOTF spectrometers is that RF power is delivered to the piezo crystal via a coaxial cable from a power amplifier located in a separate housing. This arrangement wastes electrical energy, both by attenuation in the cable and also because of losses due to impedance-matching the RF amplifier to the cable, and then the cable to the crystal. (The cable typically has an impedance of around 50 ohms, but the piezo crystal impedance is much lower and varies with frequency.) Moreover, previous AOTF spectrometers have applied more RF power to the AOTF crystal than was needed.

Since the electrical power drain from too much RF power and from using both fiber optics and coaxial cables is too great for battery power, the power supply must include circuitry to transform 120 volt AC, and a power line cord and plug must be provided. The unit then is still more difficult to transport and use.

Those of ordinary skill in the spectrometer art have been unable to achieve handheld portability by removing these power drains. Previous workers in the field apparently did not realize that the energy drains resulting from separating the components were the key problem keeping AOTF spectrometers from being portable. They placed the detector and the RF amplifier in separate housings requiring them to be connected by coaxial cable causing bulkiness and power loss, and the AOTF crystal and lamp in another housing, further hindering portability. Furthermore, they did not understand that the RF power could be reduced, allowing the RF amplifier to be placed into the same enclosure or housing as the crystal.

SUMMARY OF THE INVENTION

Accordingly, the present invention has an object, among others, to overcome deficiencies in the prior art such as noted above.

Another object is to provide a spectrometer as a handheld, portable unit.

A further object is to achieve such a portable unit by optical alignment of all optical elements.

Yet another object is to achieve the first object by placing elements adjacent one another and eliminating cables and optical fibers.

Still another object is to reduce the unit cost of an AOTF spectrometer.

A yet further object is to contain all elements within a housing and provide a window in the housing acting as a spacing element for the aligned optical elements.

The invention thus relates to a portable, hand-held AOTF spectrometer which is lightweight and small enough to be carried into the field for analyzing samples. One application includes identification of plastic waste for recycling purposes. In this case, the device can be brought in contact with the plastic waste and a measurement of the spectrum can be obtained in under one second for identifying the plastic.

The hand-held AOTF spectrometer consists of an enclosure approximately the size of a video camera, and containing a small optical bench (with light source, AOTF crystal, and reflectance detector) and a small circuit board containing all electronics (including a frequency synthesizer, A/D converter, detector preamplifier, noise reduction circuit and computer interface). In addition, a small RF amplifier is located in close proximity to the AOTF crystal, for better impedance matching and lower power consumption; by "close proximity", what is meant is no more than about 5 or 6 cm, and preferably directly adjacent one another as a single unit. The reflectance detector consist of several flat lead sulfide detectors, for example, which are facing the sample of interest in order to detect the diffusely reflected light. The computer can either be external or internal to the device. Battery operation is offered as an option. Since no fibers are used, the signal is larger and the device less expensive.

Reducing the RF power to about 1 watt allows the use of a smaller RF power amplifier with less power consumption, and makes it possible to mount it next to the crystal 122, and that mounting position eliminates the need for a coaxial cable which further decreases the power needed. This reduction in drive power reduces the optical signal from the AOTF, since the AOTF typically needs between 1 and 3 watts to reach its maximum efficiency.

However, the applicants have discovered a fact that was unknown to previous workers in the field, namely that when the drive power is reduced, the noise level is also reduced due to a reduction in electromagnetic interference (EMI) with the lower wattage amplifier (especially when the detector preamp is located close to the RF amp). Therefore, the signal to noise ratio remains approximately the same with the smaller amplifier as it was with prior-art large amplifiers, and operation of the device is not hindered. This unexpectedly high signal to noise ratio is what allows the RF amplifier to be made smaller, which in turn permits a handheld spectrometer.

The invention places a pyramid-type detector, having a generally hemispherical shape, immediately adjacent to the area on the sample where the modulated IR beam impinges. The light collection efficiency is improved and multiple detector elements (cells) can be deployed inside the pyramid. This is not possible with fiber optics, where the light collection fibers are led to a single detector element.

In addition, the invention saves power by using a frequency doubler. Previous spectrometers have used up to a 100 MHz frequency generator for driving the AOTF piezo crystal. The invention uses a 50 MHz or smaller generator which draws much less power, and then passes the 50 MHz signal through a frequency doubler. However, the doubler creates harmonics, which in turn cause the AOTF to pass optical harmonics, which are in the visible light range; this is the reason why previous workers did not use the doubler. In the present invention, a window is used which only passes IR, and blocks visible rays. Since the light makes two passes through the window in reaching the detector, the visible light is strongly attenuated and does not interfere with operation. The preferred frequency generator is a digitally-controlled synthesizer, which is faster, easier to control, and has much better stability and resolution than a voltage-controlled oscillator.

After obtaining the spectrum of the sample, the computer software can analyze the spectrum to determine the type and quantity of the sample, using previously stored calibration algorithms. The computer can then display the identification of the plastic, for example, PVC or polystyrene, for recycling purposes or for quality control purposes.

BRIEF DESCRIPTION OF THE DRAWING

The above and other objects and the nature and advantages of the present invention will become more apparent from the following detailed description of an embodiments taken in conjunction with drawings, wherein.

DETAILED DESCRIPTION OF THE PREFERRED EMBODIMENT

Here, and in the following claims:

"light" means all electromagnetic waves that can be produced, detected, or controlled by optical means, and includes infrared (IR), visible light, or ultraviolet (UV) unless otherwise specified;

"pyramid detector" means any detector with one or more light-to-electricity converting transducers deployed adjacent to a hole;

"window" means an opening or interruption in an opaque wall that allows a light beam to pass through.

Figure 1:
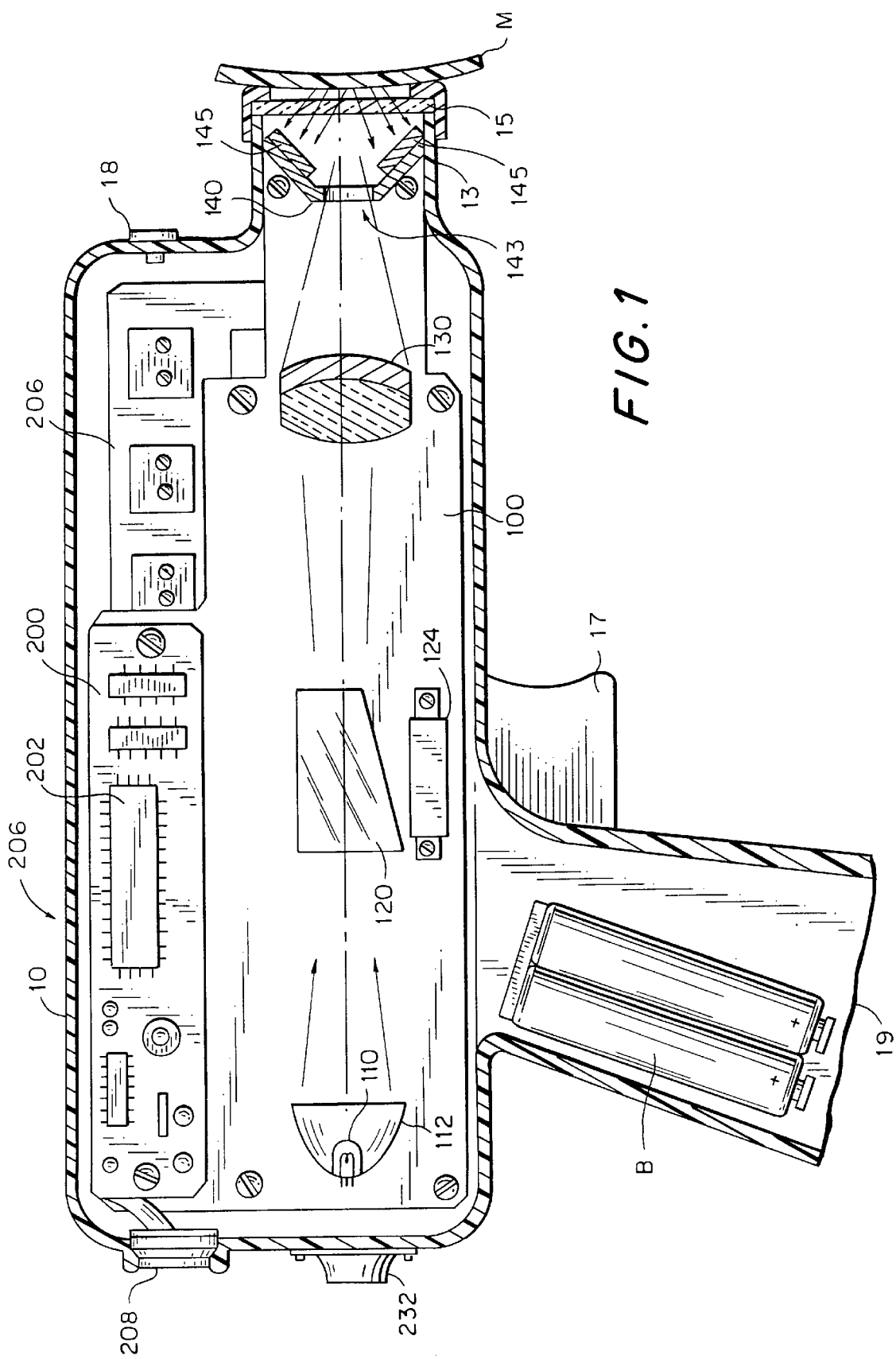
FIG. 1 is a partially schematic elevational view of the invention.
Figure 2:
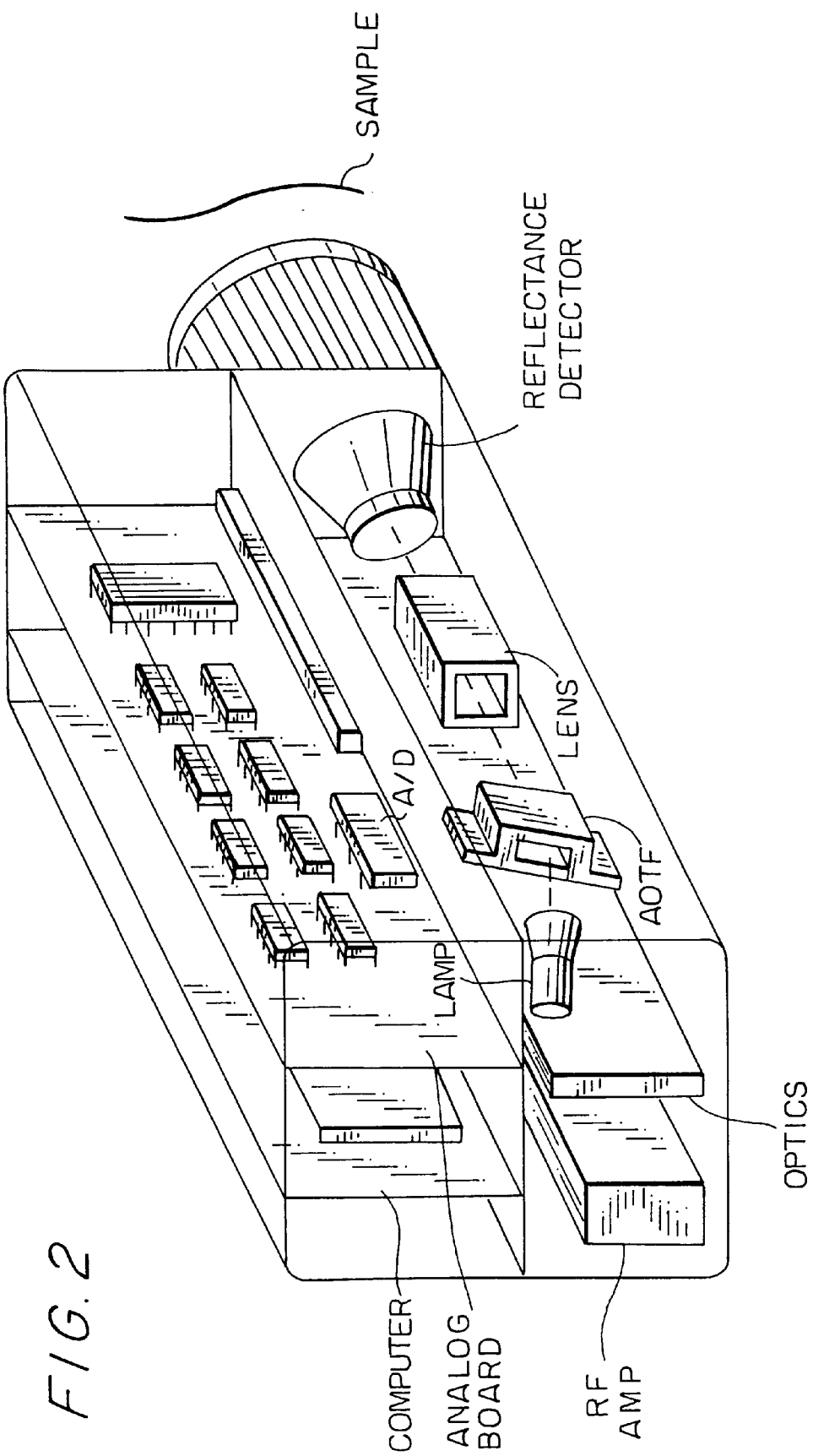
FIG. 2 is a perspective, phantom view of the invention.
Figure 3:
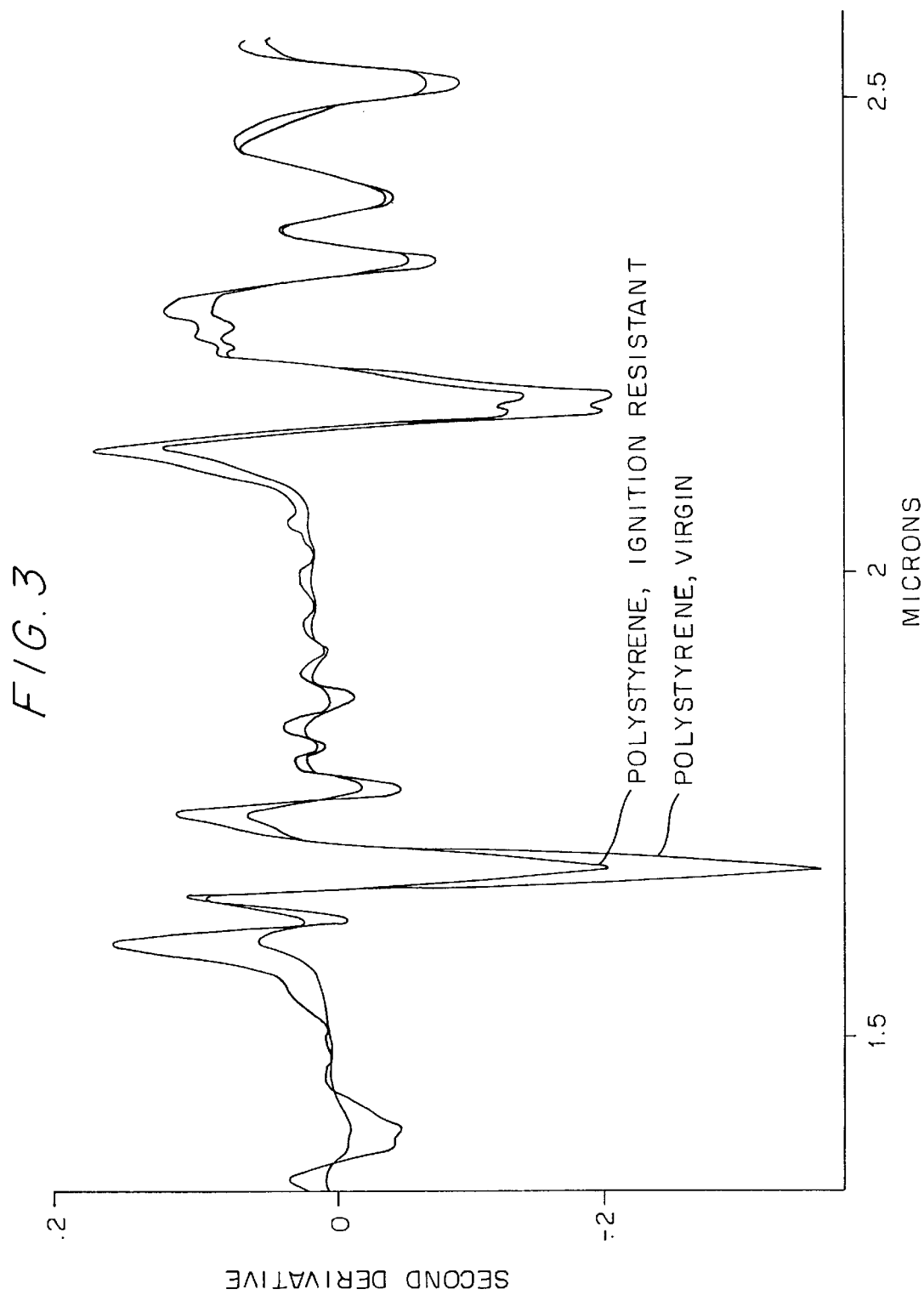
FIG. 3 is a graphical view of a light reflectance spectrum for polystyrene.

FIG. 1 shows the interior of the handheld AOTF spectrometer according to the present invention, used to identify an unknown material M. The spectrometer is housed in a molded plastic enclosure or housing 10 which includes a window 15, handle 19 with trigger 17, and battery compartment for batteries B inside the handle 19. The window 15 is preferably one which is opaque or at least partially opaque to visible light, but transparent to IR. The housing 10 is approximately the size and shape of a handheld video camera, and can include a handle. The trigger 17 is used to power the unit to or circuits of the spectrometer for making a measurement. A proximity sensor 18, such as a small sonar device or a momentary-contact switch for pressing against the material M, may be used in place of the trigger 17.

Inside the housing 10 are an optical bench 100 and a single printed circuit board 200 which contains all of the system electronics. A computer 202 for data analysis and display can either be built into the device as shown or connected remotely using a serial or parallel port 232. A computer accessed through the port 232 can also augment the on-board computer 202. The device can either be plugged into the wall by a power cord (not shown), but is preferably operated by batteries B.

The optical module consists of several optical components mounted on the bench 100, which is preferably a solid plate, e.g., formed of aluminum, approximately eight inches long by five inches wide secured inside the plastic housing. The optical components include the following elements, provided in a linear relationship: a light source or lamp 110 (a tungsten-halogen lamp, for example); an AOTF crystal and case 120; a focusing lens 130; and a reflectance detector 140. The AOTF crystal, preferably including $TeO_2$ (tellurium dioxide), is about one inch long and one-half inch wide. The AOTF 120 includes a piezo-electric transducer, preferably of LiNo, bonded to one face of the bi-refringent $TeO_2$ crystal. A small RF power amplifier 124 is mounted in close proximity to the crystal 122; it produces about 1 Watt of RF power in the frequency range from 20 to 100 MHz.

The lamp 110 is contained within a parabolic mirror 112 in order to collimate the beam. This beam then passes through the AOTF crystal 120, and emerges as a tuned, narrow-band infrared beam approximately 8 by 8 mm in size. This beam passes through the lens 130, which focuses the beam through the window 15, onto the sample M to be analyzed.

At the end of the optical bench is mounted a reflectance detector 140. This detector may include up to four or even more lead sulfide (PbS) or lead selenide (PbSe) flat detector elements or transducers 145, each about 10 by 10 mm in size and facing the sample through the window 15. The detectors are arranged on the inner surface of a 45 degree pyramid or cone. The cone has a hole 143 at the apex for the light beam to pass through. The base of the pyramid faces the sample. Therefore, the infrared beam strikes the sample, and the diffusely reflected light from the sample (indicated by arrows in FIG. 1) is detected by the detector elements 145.

Figure 4:
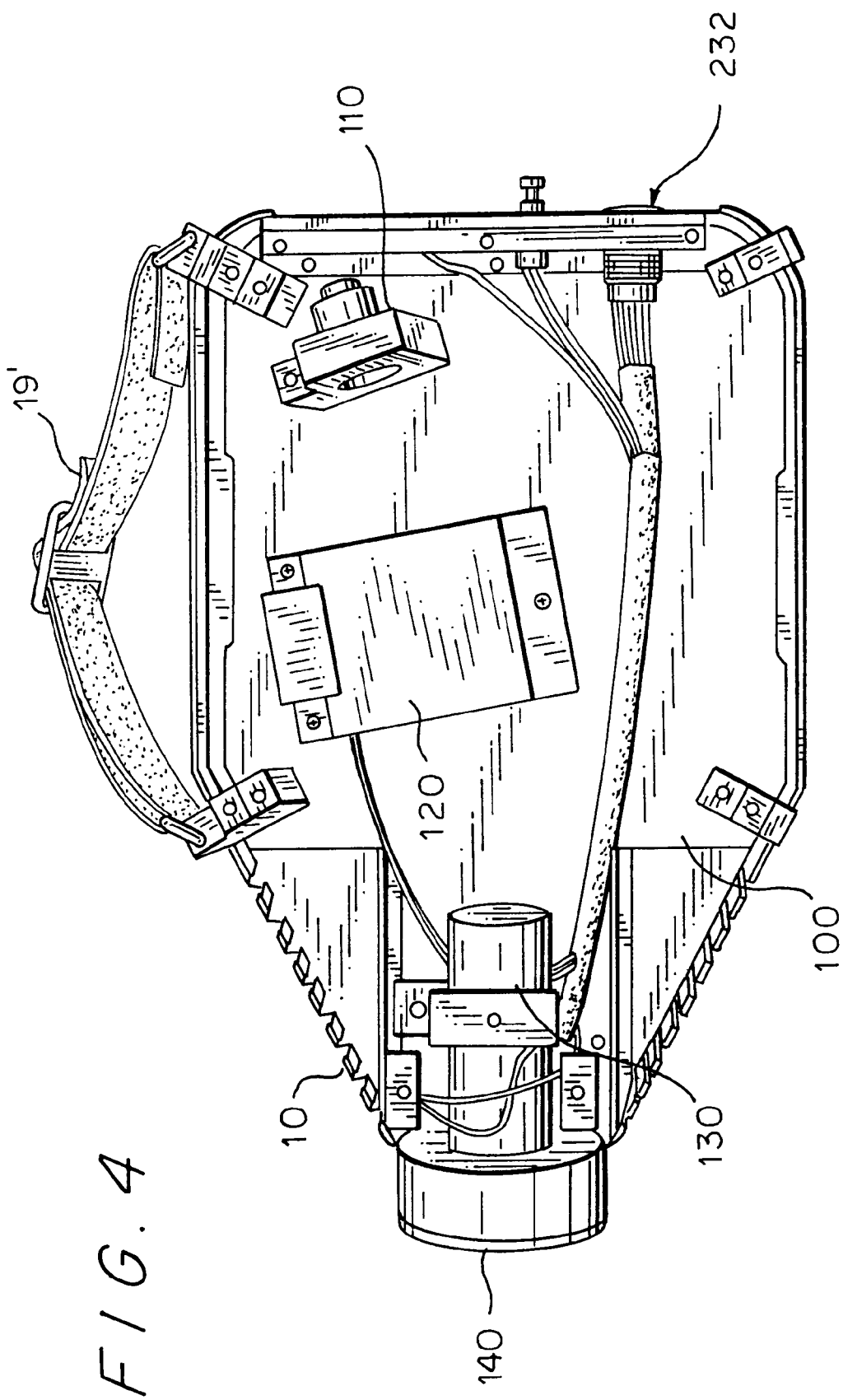
FIG. 4 is a plan view of a realized embodiment of the invention.

FIG. 4 shows a realized embodiment of the invention, with a carrying strap 19', and some other elements shown in FIG. 1.

Figure 5:
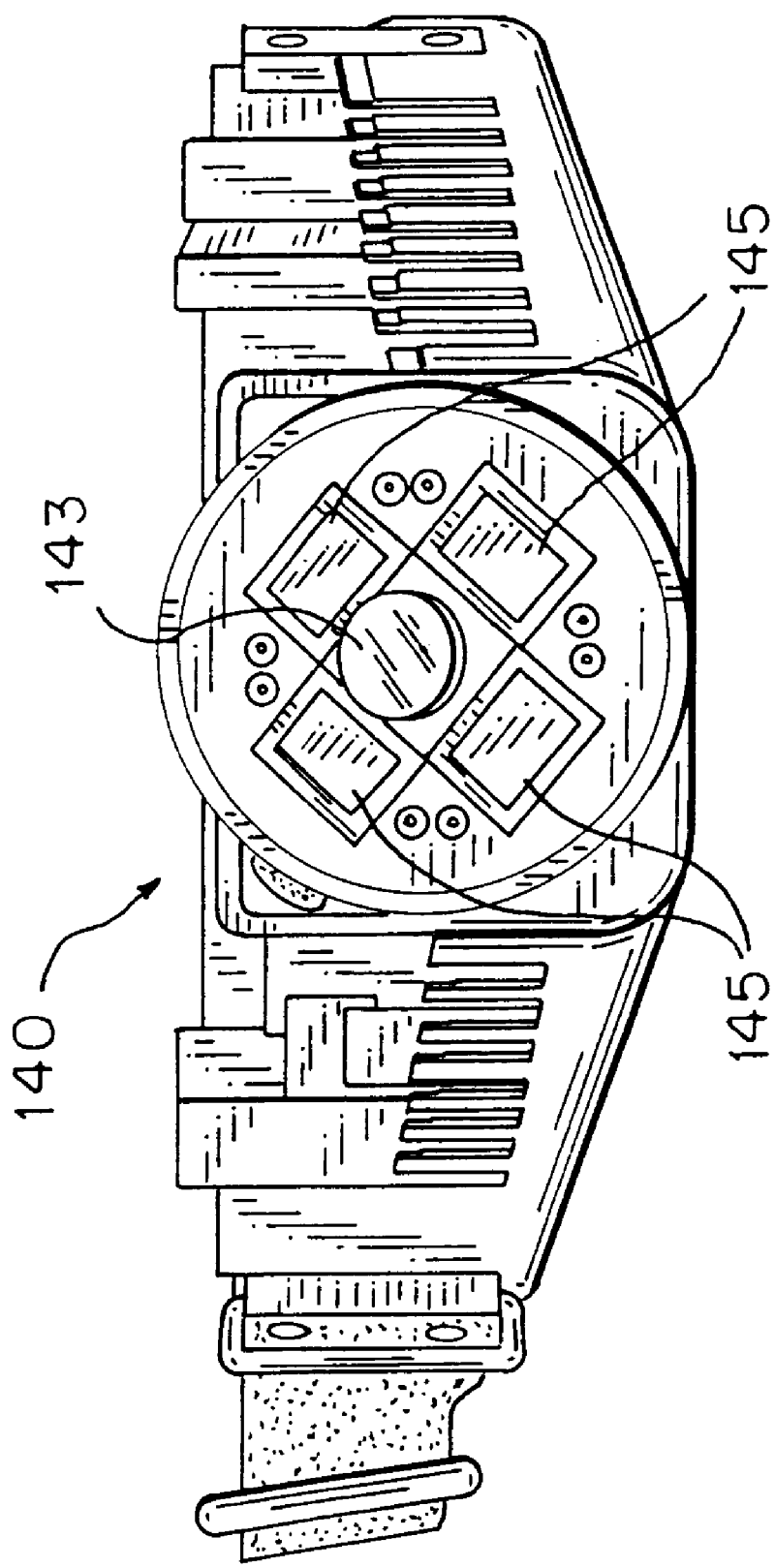
FIG. 5 is an elevational view of the embodiment of FIG. 4.

FIG. 5 is an end view of a realized embodiment of FIG. 4, showing the hole 143 and detector elements 145 as seen from outside the housing 10.

As indicated above, the housing includes the window 15, which in the preferred embodiment is a transparent element having broad-band IR transmission but little visible transmission; it appears black. The optical properties of the window 15, like those of the other optical elements, are compensated for automatically when the device is calibrated using a pure white ceramic material.

The window 15 is set at the end of an optional housing extension 13; the extension 13 may be placed directly against the sample M surface to obtain the preferred spacing of the surface from the optical bench 100 and its components, so as to maximize the light efficiency.

The small printed circuit board 200 mounted above the optical bench 100 contains all of the system electronics 204, including: a digitally-controlled frequency synthesizer (used to generate the RF frequencies to tune the AOTF), a detector preamplifier and bias voltage, an A/D converter, and computer interface (e.g., RS-232). In addition, there is an amplitude modulator (and de-modulator) circuit which modulates the RF signal at about 5 kHz for improved signal to noise ratio. The frequency synthesizer is preferably a lower-frequency generator (e.g., up to 50 MHz) driving a doubler; this arrangement uses less power.

Having the circuit board in close proximity to the detector and optics has several advantages: smaller size, lower noise, and less expense since fewer cables and connectors are used.

It is also possible to include, besides a microcomputer circuit 202, a keypad 206 (the back side is shown on the inside of the housing 100 in FIG. 1); and a display 208 on the housing, for displaying alphanumeric messages such as "polystyrene: 25%". These allow an external notebook computer to be eliminated. The complete unit can then be battery powered by batteries B for complete portability.

Advantages

The arrangement of the AOTF 120 and a built-in reflectance detector 140 on one single small optical bench leads to many advantages, as discussed below.

Combining the optical elements, RF amplifier 124, and reflectance detector 140 together on a small optical bench 100 and within a handheld case 100, improves the signal to noise ratio. The signal is larger because no fiber optics are needed (the instrument can be brought directly up to the sample of interest). Less power consumption is necessary, allowing for battery operation. And, the device is very rugged and relatively inexpensive to produce compared to other designs. Placing the RF amplifier 124 adjacent to the piezo crystal of the AOTF 120 (instead of in a separate enclosure and connected by a cable) results in better impedance matching, lower power consumption—up to five times less—and smaller size.

Reducing the RF power to about 1 watt saves power as well.

In order to further reduce power consumption, the electronic circuitry is placed in a "sleep" mode during the "off" cycle of the AOTF amplitude modulation.

In order to reduce the temperature drift of AOTF wavelength selectivity (by an order of magnitude), the clock generator (oscillator) for frequency synthesis is made temperature dependent with the value of the AOTF temperature dependency, but with an opposite sign. The RF synthesizer output frequency linearly depends on the clock generator frequency. Both the clock and the AOTF are placed into the same small sealed case 120, close to each other, resulting in each having the same temperature variation. This compensates the AOTF thermal wavelength drift.

By eliminating the optical fibers, the large RF amplifier, and various connectors and cables, and by using a lower wattage lamp (and smaller power supply), the cost of parts is reduced. In addition, by reducing the number of optical and electronic components, and simplifying the overall construction by using a single plastic case and optical baseplate (bench), the assembly time is reduced. This enables the device to be produced in large volume at much lower cost compared to previous large and complicated AOTF spectrometers. The cost of in instrument according to the present invention is projected to be less than $15,000, or about three times cheaper than currently-available AOTF spectrometers.

The straight-line optical alignment of the lamp 110, AOTF 120, lens 130, and the hole 143 of the detector 140, and their fixed optimal spacing from the window 15 of the housing 10, provide the maximum optical efficiency with less light loss than in the prior-art designs. For example, the lens 130 is able to focus the maximum amount of the available light onto the sample in an area that is optimal for pickup by the detectors 145. By mounting all the elements on a bench, eliminating fiber optics, the present invention cuts the power needed for the lamp by an order of magnitude, making a handheld unit possible.

By use of a detector sensitive in the UV and visible regions (such as silicon) and by using a clear window, then the ultraviolet and visible reflectance spectrum may also be obtained with the device. Applications include, for example, determining the color of paint, vegetation, and minerals in the field.

The transmission spectrum of a sample may be obtained using the device by placing a mirror in back of the sample to reflect the transmitted beam from the AOTF back again through the sample and onto the detector. Applications include, for example, identification of clear plastic bottles or liquids of various types. (We have used this method to identify discarded soda bottles.)

EXAMPLE

An operational system, shown in FIG. 4, was built and used to identify plastics for recycling purposes. Unknown plastic samples were test scanned with the instrument, which had been previously calibrated with a set of known samples and with a ceramic reference sample. The near-infrared diffuse reflectance spectrum was measured in under one second, the spectrum was normalized using the reference spectrum, and a software algorithm identified the type of plastic. Since the detector could be brought up directly to the sample, it was not necessary to use fiber optics, which resulted in a larger signal. Types of plastic that were test identified included PVC, polystyrene, polypropylene, PET, etc. The small size and portability of the device enabled it to be carried into the field. Due to the higher signal level obtained without fibers, the device was able to identify darkly colored plastic samples in addition to white samples.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. The means and materials for carrying out various disclosed functions may take a variety of alternative forms without departing from the invention. It is to be understood that the phraseology or terminology employed herein is for the purpose of description and not of limitation.

What is claimed is:

1. A handheld device for light reflectance measurements of samples, the device comprising:

a housing including a window through a housing wall;

a reflectance detector aligned with the window of the housing;

an acousto-optic tunable filter (AOTF);

a light source;

means for generating a light beam, having a swept wavelength, from the light source and the tunable filter;

alignment means for optically aligning the beam with the window and emitting the beam therefrom; and electric circuit means for accepting an electric signal from the detector;

wherein the reflectance detector, the filter, the light source, the means for generating, and the alignment means are disposed inside the housing.

2. The device according to claim 1, which is battery powered.

3. The device according to claim 1 wherein the window at least partly blocks visible light but is transparent to IR.

4. The device according to claim 1, wherein the means for generating a light beam comprises an RF amplifier in close proximity to the AOTF crystal.

5. The device according to claim 4, wherein the RF amplifier has an output of less than 3 watts.

6. The device according to claim 5, wherein the RF amplifier has an output of less than 1.5 watts.

7. The device according to claim 1, wherein the housing includes a handle.

8. The device according to claim 1, wherein the housing includes a trigger switch.

9. The device according to claim 1, wherein the housing includes a proximity sensor.

10. The device according to claim 1, wherein the alignment means includes a lens.

11. The device according to claim 5, wherein the alignment means for optically aligning the beam with the window includes the reflectance detector, the acousto-optic tunable filter, the light source, and the lens being mounted on an optical bench within the housing.

12. The device according to claim 11, wherein the means for generating a light beam comprises an RF amplifier mounted on the optical bench.

13. The device according to claim 1, wherein the device includes means for analyzing plastic.

14. The device according to claim 1, wherein the detector includes a hole aligned with the window of the housing and at least one detector-element transducer for converting light intensity to an electric signal.

15. The device according to claim 14, wherein the transducer is disposed on an interior surface of the detector surrounding the hole.

16. The device according to claim 15, wherein the transducer is offset from the swept wavelength beam so as to collect reflected beam light from a sample adjacent the housing window.

17. The device according to claim 1, wherein the AOTF thermal wavelength drift is compensated.

18. The device according to claim 1, wherein the electric circuit means includes computer means for determining a spectrum and analyzing data.

19. The device according to claim 18, wherein the housing encloses the electric circuit means.

20. The device according to claim 18, comprising a display disposed on an exterior surface of the housing and wherein the means for analysing data includes means for displaying sample identifications and proportions on the display.

21. The device according to claim 20, wherein the computer means for determining a spectrum and analyzing data includes means for determining a reflectance spectrum, matching the reflectance spectrum to one of a stored catalog of material spectra, and indicating on the display a type of material identified as matching the reflectance spectrum.

22. The device according to claim 1, wherein the means for generating a light beam having a swept wavelength includes an "off" cycle of AOTF amplitude modulation, and the electric circuit means includes means to reduce power consumption by going into a "sleep" mode during the "off" cycle of the AOTF amplitude modulation.

23. The device according to claim 1, wherein the electric circuit means includes means for coupling to a computer for determining a spectrum and analyzing data.

24. A method of identifying a material composition of a sample, comprising:

(a) providing a handheld device for light reflectance measurements, the device comprising:

a housing including a window through a housing wall, the window being disposed on the housing in an exterior position such that the window may be placed against a surface of the sample;

a lens mounted in the housing to concentrate light onto an area on the surface of the sample;

a reflectance detector adjacent the area;

a lamp aligned with the lens to provide the light on the area of the surface of the sample; and optical analysis means for determining the material composition, comprising an acousto-optic tunable filter disposed between the lamp and the lens, and electronic means for driving the filter at a swept frequency, comparing a reflectance spectrum of the sample with a reference spectrum, determining the material composition, and outputting an analysis of the material composition; wherein the lamp, the lens, the tunable filter, and the window are aligned on a common optical axis, the detector includes a hole aligned on the common optical axis, and the detector includes at least one detector element offset from the optical axis; and (b) placing the window against the sample.

25. The method according to claim 24, wherein the sample is transparent and including a step of placing a mirror adjacent a back side opposite to a front side of the sample where the window is placed.

* * * * *